(12) United States Patent
Boysen et al.

(10) Patent No.: US 11,737,653 B2
(45) Date of Patent: Aug. 29, 2023

(54) ENDOSCOPE COUPLER FOR A CAMERA AND METHOD FOR COUPLING AND DECOUPLING AN ENDOSCOPE WITH A CAMERA BY MEANS OF AN ENDOSCOPE COUPLER AS WELL AS CAMERA WITH ENDOSCOPE COUPLER

(71) Applicant: ATMOS MedizinTechnik GmbH & Co. KG, Lenzkirch (DE)

(72) Inventors: Bjoern Boysen, Lenzkirch (DE); Carsten Reinhardt, Lenzkirch (DE)

(73) Assignee: ATMOS MedizinTechnik Gmbh & Co. KG, Lenzkirch (DE)

( * ) Notice: Subject to any disclaimer, the term of this patent is extended or adjusted under 35 U.S.C. 154(b) by 0 days.

(21) Appl. No.: 16/879,313

(22) Filed: May 20, 2020

(65) Prior Publication Data
US 2020/0367728 A1    Nov. 26, 2020

(30) Foreign Application Priority Data
May 21, 2019   (DE) ............... 10 2019 113 435.8

(51) Int. Cl.
*A61B 1/00*  (2006.01)
*A61B 1/05*  (2006.01)
*A61B 1/04*  (2006.01)

(52) U.S. Cl.
CPC ...... *A61B 1/00126* (2013.01); *A61B 1/00052* (2013.01); *A61B 1/00096* (2013.01);
(Continued)

(58) Field of Classification Search
CPC . A61B 1/00126; A61B 1/00096; A61B 1/053; A61B 1/042; A61B 1/00128;
(Continued)

(56) References Cited

U.S. PATENT DOCUMENTS 5,707,340 A * 1/1998 Hipp ............... G02B 23/2484
396/17
2006/0220381 A1* 10/2006 Gill .................... F16L 21/06
285/308
(Continued)

FOREIGN PATENT DOCUMENTS

DE         19712645        10/1998
DE       102012005037        9/2013
(Continued)

*Primary Examiner* — Ryan N Henderson
*Assistant Examiner* — Sung Ham
(74) *Attorney, Agent, or Firm* — Akerman LLP; Peter A. Chiabotti

(57) ABSTRACT

An endoscope coupler for a camera, with a proximal end of the endoscope coupler for the disposition on the camera, with a camera securement mechanism for securing the endoscope coupler on the camera and with an endoscope head-receiving region for the at least partial reception of an endoscope head when an endoscope is coupled with the camera, wherein the endoscope head-receiving region is accessible across an access for the endoscope head from the direction of a distal end of the endoscope coupler, and with a movably supported jaw that secures the endoscope on the endoscope coupler. The jaw can be loaded with a spring force such that at least one region of the jaw is pressed into the access and blocks the access.

10 Claims, 9 Drawing Sheets

(52) U.S. Cl.
CPC ...... *A61B 1/00121* (2013.01); *A61B 1/00195* (2013.01); *A61B 1/042* (2013.01); *A61B 1/053* (2013.01)

(58) Field of Classification Search
CPC ............ A61B 1/00066; A61B 1/00105; A61B 1/00052; A61B 1/00121; A61B 1/00195; G02B 23/2476
USPC ........................................................ 600/112
See application file for complete search history.

(56) References Cited

U.S. PATENT DOCUMENTS

| | | | |
|---|---|---|---|
| 2007/0010707 A1* | 1/2007 | Leiner | A61B 1/00126 600/167 |
| 2011/0317274 A1* | 12/2011 | Faber | A61B 1/00126 359/643 |
| 2015/0105620 A1 | 4/2015 | Oginski et al. | |
| 2016/0128550 A1 | 5/2016 | Laser et al. | |
| 2020/0084344 A1* | 3/2020 | Ohno | H04N 5/2251 |

FOREIGN PATENT DOCUMENTS

| | | |
|---|---|---|
| DE | 102014222880 | 5/2016 |
| DE | 102015122499 | 6/2017 |
| FR | 2793567 | 11/2000 |
| WO | 2013/156024 | 10/2013 |

\* cited by examiner

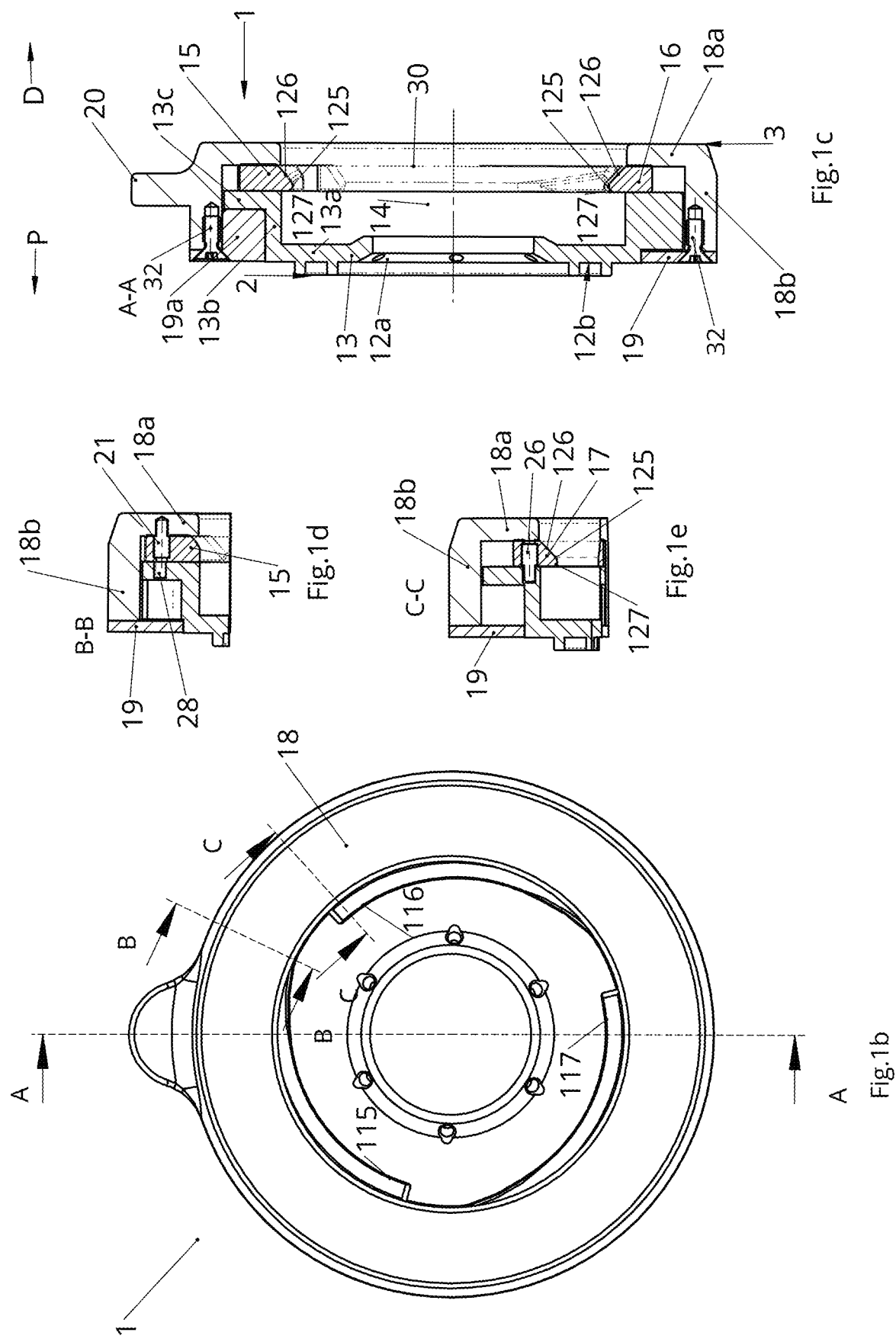

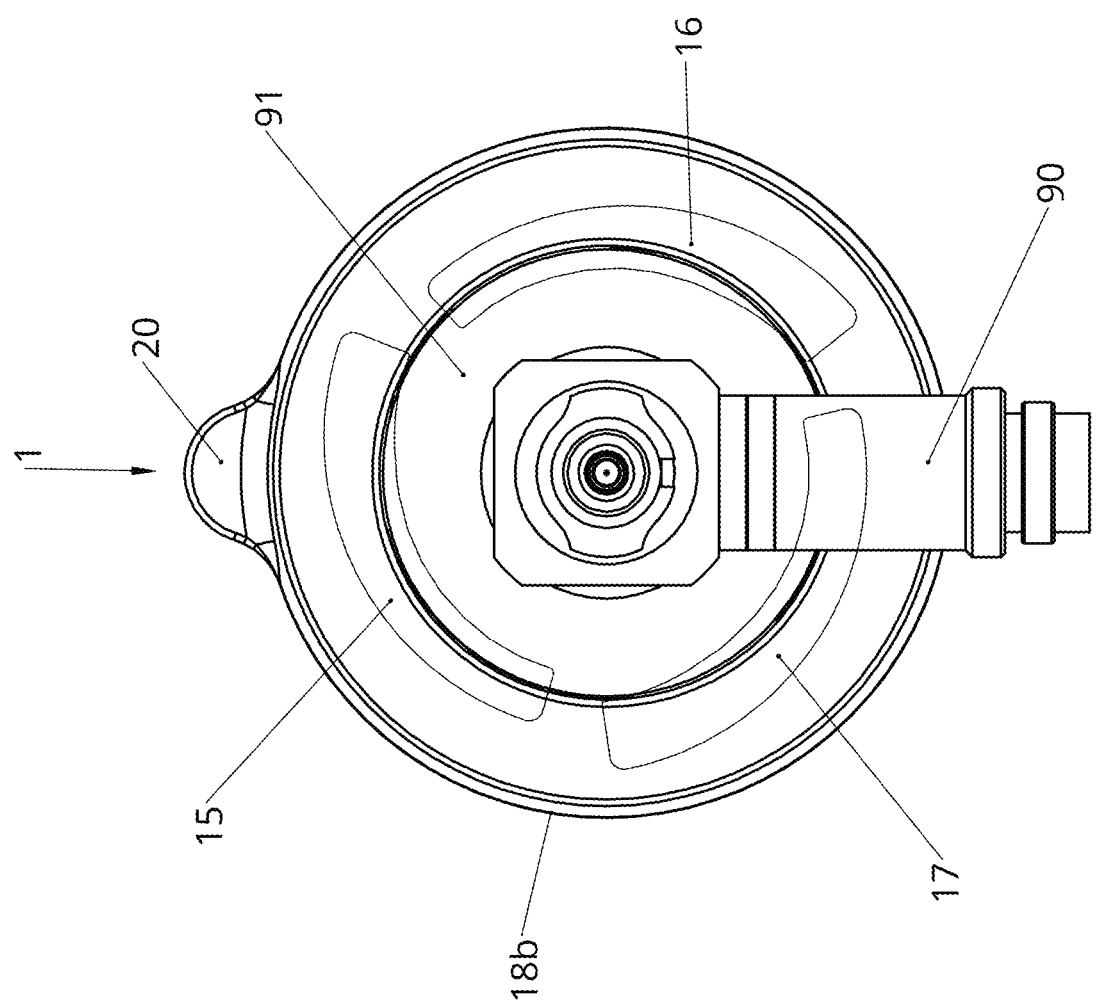

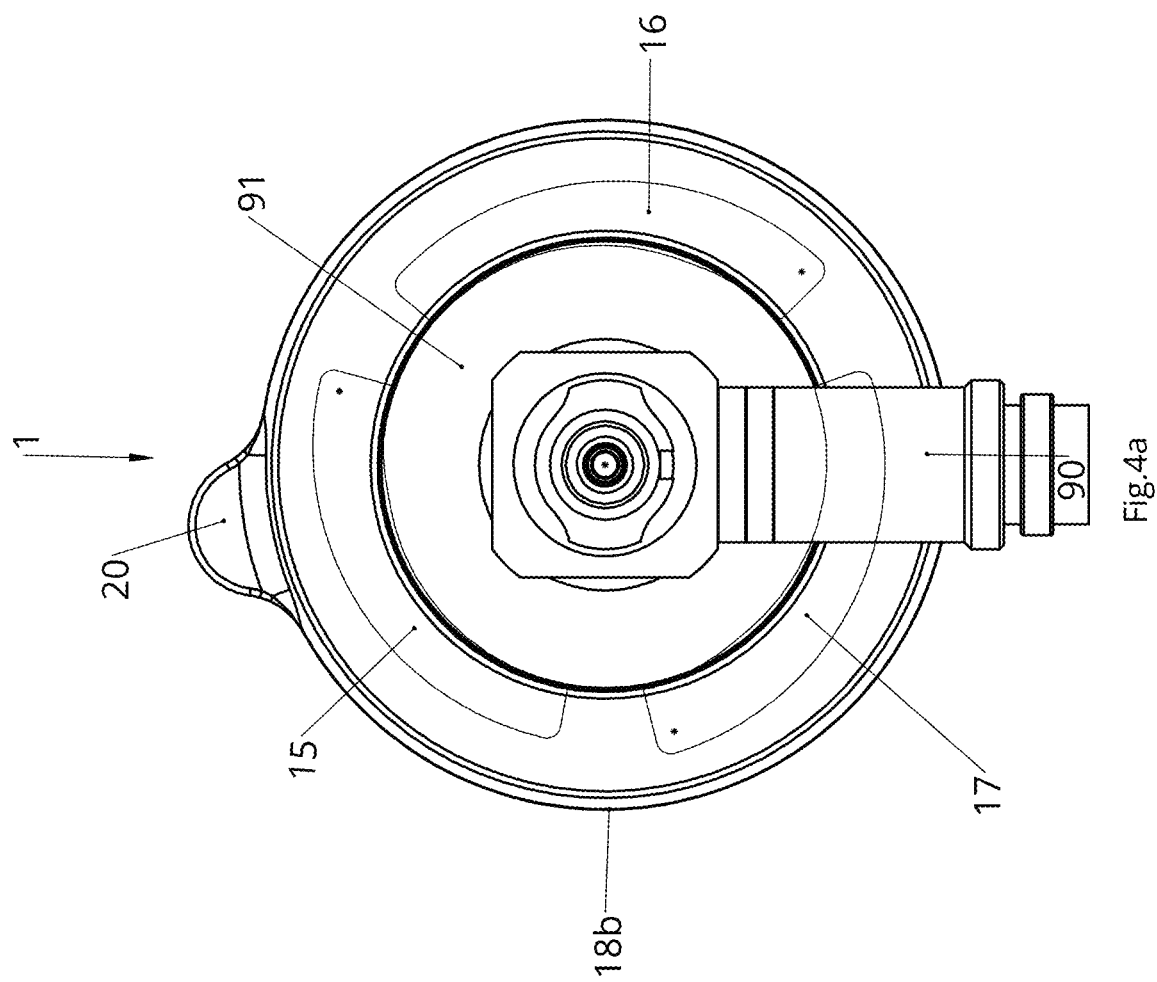

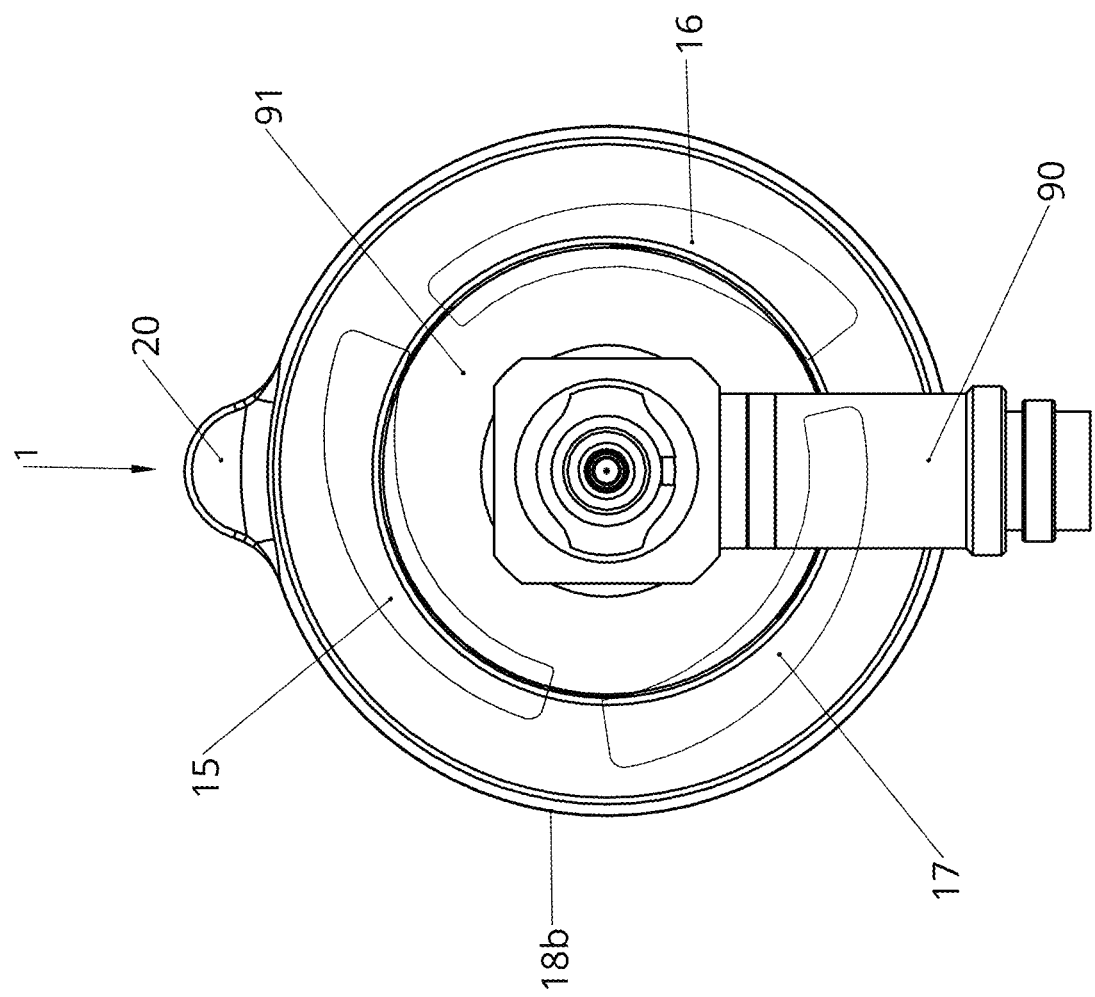

ENDOSCOPE COUPLER FOR A CAMERA AND METHOD FOR COUPLING AND DECOUPLING AN ENDOSCOPE WITH A CAMERA BY MEANS OF AN ENDOSCOPE COUPLER AS WELL AS CAMERA WITH ENDOSCOPE COUPLER

CROSS-REFERENCE TO RELATED APPLICATIONS

This application claims priority to German Patent Application No. 10 2019 113 435.8, filed May 21, 2019, which is incorporated by reference in its entirety.

SUMMARY

Endoscopic methods represent one of the most important methods for investigating—in particular visually—the inside of the human body and, if appropriate, for initiating treatment. To document the diagnosis obtained during the endoscopy, but also that of a possible treatment, cameras are herein used which are detachably connected with the proximal end region of the endoscope with a retaining mechanism by means of an endoscope coupler.

Such endoscope couplers are already disclosed in prior art, for example in DE 10 2012 005 037 A1, WO 2013/156024 A1 or DE 10 2014 222 880 A1. However, of disadvantage in the known endoscope couplers is that the retaining mechanism for the detachable connection requires comparatively high operating efforts, since in each instance a fixing means must be detached and, in particular, the operation using only one hand is not possible at all or only with great difficulty.

The application therefore addresses the problem of providing an endoscope coupler operable with lesser operating expenditures and, in each instance, a method for coupling an endoscope with a camera by means of an endoscope coupler, or for decoupling an endoscope from a camera by means of an endoscope coupler, which simplifies the coupling or decoupling. One problem addressed by the application is further to provide a camera which comprises such an endoscope coupler to be operated with lower operating expenditures.

This problem is resolved through an endoscope coupler of some embodiments herein as well as through a camera of some other embodiments herein. Advantageous further developments of the endoscope coupler or of the method are subject matter of the dependent claims.

The endoscope coupler for a camera has a proximal end for the disposition on the camera, a camera securement mechanism for securing the endoscope coupler on the camera, and an endoscope head-receiving region for the at least partial reception of an endoscope head when an endoscope is coupled with the camera, wherein the endoscope head-receiving region comprises an access for the endoscope head from the direction of the distal end of the endoscope coupler. The endoscope coupler, furthermore, comprises an endoscope-fixing mechanism for securing the endoscope on the endoscope coupler.

The camera securement mechanism can be, for example, a conventional threaded connection, a bayonet closure, a section pressure-compressed with the camera or a click closure.

The endoscope-fixing mechanism comprises at least one movably supported jaw upon which a spring force acts such that at least one region of the jaw is pressed into the access and blocks the access, wherein at least the region of the jaw projecting into the access is shaped such that its distal section tapers in the direction toward the distal end of the endoscope coupler such that a pressure onto the distal section of the region, projecting into the access, of the jaw in the direction toward the proximal end of the endoscope coupler generates a force counteracting the spring force.

It becomes possible in this way to press the endoscope head, in particular an eye piece of the endoscope head, preferably corresponding to DIN 58105, simply in the direction onto the proximal end of the endoscope coupler against the jaws implemented thusly.

In particular in the case in which more than one such jaw is available, which is preferred, especially preferred is an embodiment with at least three such jaws [sic: at least one such jaw of up to three], and if the jaws are implemented identically with respect to their geometry, the self-centering of the endoscope head can be attained immediately at the beginning of contact.

Due to the tapering section of the jaw, subsequently upon pressure contact a force component is generated which counteracts the spring force in the radial direction and lastly overcomes it such that the jaw is pressed increasingly further out of the access to the endoscope head-receiving region and the endoscope head moves further in the direction to the endoscope head-receiving region until the jaw clears the access completely and the endoscope head enters into the endoscope head-receiving region.

Since the endoscope head or its eye piece tapers in the distal direction, the jaw starts to slide again into the access during its further penetration of the endoscope head into the endoscope head-receiving region and gradually starts to block the movement of the endoscope head in the distal direction, until lastly the endoscope head abuts the bottom of the endoscope head-receiving region.

In this state, and as a function in particular of the spring force acting upon the jaw, at best only a rotation of the endoscope head relative to the endoscope coupler can now take place. In so far, the endoscope head is at least fixed against a displacement.

It is especially preferred for the endoscope coupler to comprise also a detachment mechanism, upon the actuation of which regions, projecting into the access, of the jaw are moved out of the access or can be moved out of the access. This can be attained in particular thereby that the detachment mechanism is structured such that, upon its actuation, it reduces the spring force loading of the jaw.

The detachment mechanism is herein preferably structured such that it is initiated through a rotation in the circumferential direction of the endoscope coupler. Such a rotation can readily be completed with one hand and can subsequently detach all jaws simultaneously, while detachment mechanisms that rely on a translational movement are in general only able to effect the detachment of a single jaw.

If, in addition, at least the region of the jaw projecting into the access is formed such that its proximal section tapers more steeply toward the proximal end of the endoscope coupler than does the distal section in the direction toward the distal end of the endoscope coupler, on one hand, the immobilization of the endoscope head, in particular of an eye piece, is improved after it has been introduced into the endoscope head-receiving region.

On the other hand, it can be achieved in this manner that the detachment process also proceeds under tight control and does not occur immediately following an unintentional actuation of the detachment mechanism, but only when an additional pull in the distal [direction] is exerted onto the endoscope head. The mechanism of action is herein similar to the introduction of the endoscope head, the difference in the inclinations in the tapering, however, leads to the fact that very much higher tensile forces would be necessary to press the jaw out of the access to the endoscope head-receiving region if the spring force loading of the jaws is not reduced through the actuation of the detachment mechanism. However, the detachment mechanism can be laid out such that a residual spring force loading of the jaw remains which must be actively overcome through pulling.

According to a preferred further development, the movably supported jaw is supported on one of its side rotatably about an axis extending parallel to the direction of introduction of the endoscope head. It is herein especially preferred when this axis, in turn, is supported in an, in particular, annular structural part which is rotatable jointly with the jaw in the circumferential direction. For example, through the cooperation with a suitable assembly means or connecting link, a detachment mechanism can be realized in an especially simple manner which can be initiated through rotation and preferably single-handedly.

To enable such rotatability, also that of the supported axis with the jaw disposed thereon, in the circumferential direction, it is advantageous for the support, rotatable about an axis extending parallel to the introduction direction of the endoscope head, to be realized by a first pin which projects beyond the jaw either only in the direction toward the distal end of the endoscope coupler or only in the direction toward the proximal end of the endoscope coupler.

A guidance, with which the engagement of the jaw into the access can be controlled, can be realized in particular thereby that the movably supported jaw is displaceably supported on its other side in a guide groove. Such a type of guidance can be realized especially simply if the support displaceable in the guide groove is implemented through a second pin which only projects beyond the jaw in the direction that is opposite to the direction in which the first pin, through which the support takes place that is rotatable about the axis extending parallel to the direction of introduction of the endoscope head, projects beyond the jaw.

An especially advantageous feasibility of realizing the pressure loading by means of a spring force comprises that the spring force loading takes place through a spring, in particular through a compression spring, disposed in the guide groove. In this configuration it can, in particular, also be attained that, after its actuation, the detachment mechanism can automatically be guided back again into the locked position.

The method for coupling an endoscope to a camera using an endoscope coupler comprises the steps of securing the endoscope coupler on the camera and securing the endoscope head on the endoscope coupler, and is distinguished thereby that the coupling of the endoscope head to the endoscope coupler is completed by merely exerting pressure. Therewith an extremely simple coupling feasibility is provided which can also be carried out with one hand.

Herein is a especially preferred method in which as the endoscope coupler an endoscope coupler, preferably according to one of the above described further developments, is utilized.

The method for decoupling an endoscope from an endoscope coupler is distinguished thereby that the method comprises the actuation of precisely one detachment mechanism which acts onto all fixing means retaining the endoscope on the endoscope coupler. Hereby a simple decoupling process is enabled which, in particular as a rule, can also be completed using only one hand.

It is herein especially preferred if as the endoscope coupler an endoscope coupler with a detachment mechanism is utilized, wherein the detachment mechanism is preferably actuated through a rotational movement in the circumferential direction of the endoscope coupler.

The camera is distinguished by an endoscope coupler. In a preferred further development, the endoscope coupler is fixedly connected with the camera, in particular held together under pressure and/or through threaded connections.

It is herein especially preferred for a portion of the optical system of the camera to be disposed on the endoscope coupler. An especially efficient structural space utilization is hereby feasible.

BRIEF DESCRIPTION OF DRAWINGS

In the following, the application will be explained in detail in conjunction with Figures showing example embodiments. In the drawing depict:

FIG. 1b: a top view onto the endoscope coupler of FIG. 1a,

FIG. 1c: a first cross section through the endoscope coupler of FIG. 1b along the sectional line A-A, FIG. 1d: a second cross section through the endoscope coupler of FIG. 1b along the sectional line B-B, FIG. 1e: a third cross section through the endoscope coupler of FIG. 1b along the sectional line C-C, FIG. 3a: a view of the endoscope coupler and endoscope head of FIG. 2 immediately before the coupling, FIG. 4a: a view of the endoscope coupler and endoscope head of FIG. 2 during the coupling, FIG. 5a: a view of the endoscope coupler and endoscope head of FIG. 3 in the coupled state.

DETAILED DESCRIPTION

Unless stated otherwise, identical components of identical embodiments of the endoscope coupler are identified by the same reference numbers in the Figures. To enhance clarity, however, not all reference numbers are entered in all Figures.

Figure 1A:
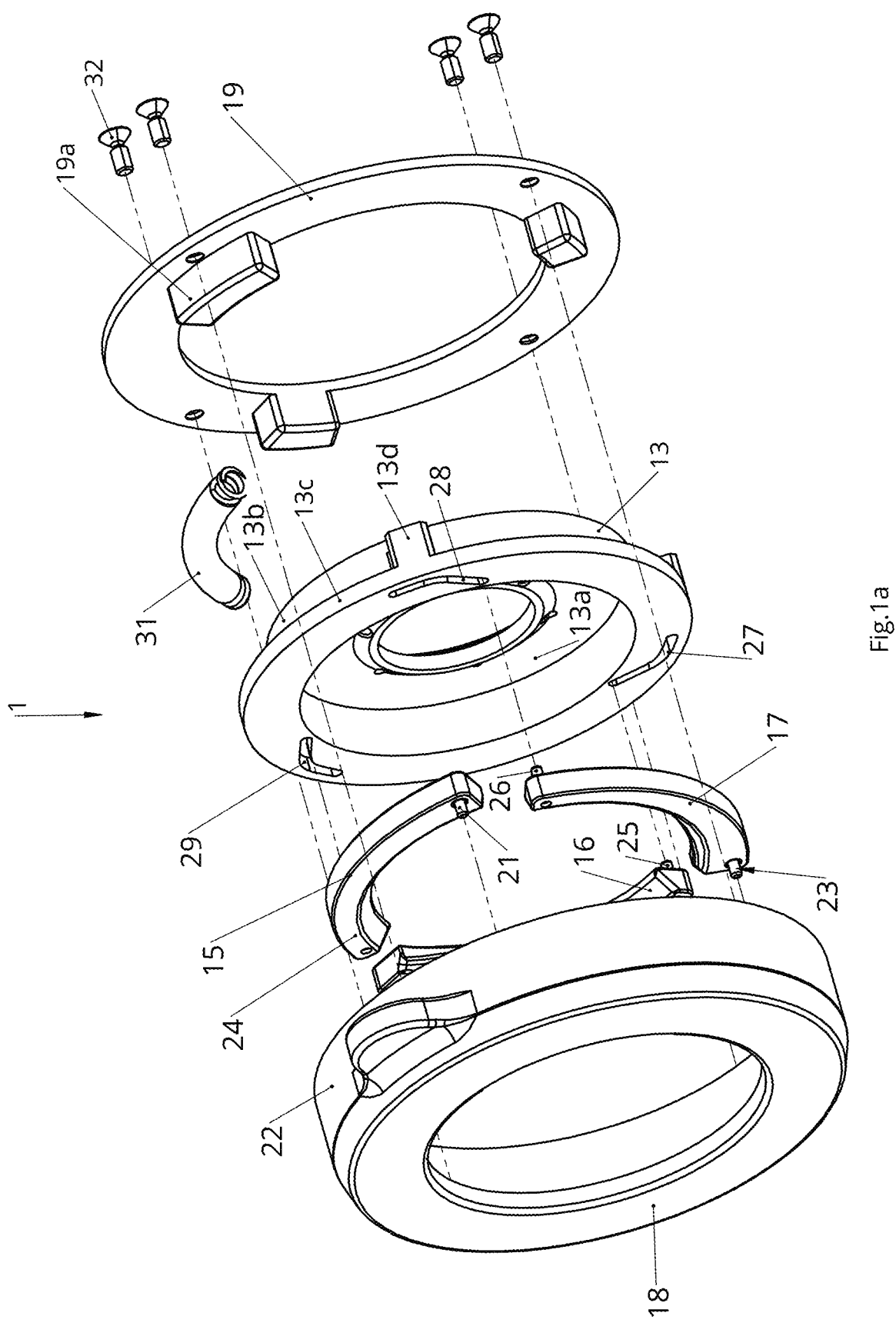
FIG. 1a: an exploded depiction of an endoscope coupler.

FIGS. 1a to 1e show an endoscope coupler 1 with jaws 15, 16, 17. FIG. 1a shows in particular an exploded depiction, FIG. 1b a top view onto the endoscope coupler viewed in the direction of introduction of an endoscope head 90 to be coupled, FIG. 1c a cross section through an endoscope coupler 1 along the line A-A, which corresponds to a diameter of the endoscope coupler 1, FIG. 1d a half-side cross section through the endoscope coupler 1 along line B-B which defines a sectional plane through a first of the bearing section of jaws 15, 16, 17 using jaw 15 as an example, and FIG. 1e shows a half-side cross section through the endoscope coupler 1 along line C-C which defines a sectional plane through a second of the bearing section of jaws 15, 16, 17 using jaw 16 as an example.

A synopsis of these Figures makes evident that the endoscope coupler 1, as can be seen especially clearly in FIG. 1c, comprises a proximal end 2 for the disposition of the endoscope coupler 1 on a not shown camera and with a distal end 3 opposite to the proximal end 2. The definition can be derived directly therefrom of the proximal direction P and the distal direction D, each entered as arrows for illustration.

As the synopsis of FIGS. 1a and 1c shows especially clearly, the endoscope coupler 1 comprises a pot-shaped endoscope reception 13 with bottom 13a, circumferential side wall 13b and a broad edge region 13c, extending parallel to the bottom 13a, extending from the distal end of the edge region 13c outwardly in the radial direction. The pot-shaped endoscope reception 13 further comprises bearing sections 13d which, in this example, are implemented as local thickenings, projecting in the form of blocks radially outwardly, of the edge region 13c.

The interior volume of the pot-shaped endoscope reception 13 forms the endoscope head-receiving region 14. At the bottom 13a of the pot-shaped endoscope reception 13 is provided an opening through which the image can reach the camera from the endoscope. Optionally optical elements, for example a lens system, can also be disposed here.

In this embodiment example, further, on bottom 13a are formed on a camera securement mechanism 12a comprising openings for threaded connections of the endoscope coupler 1 with the camera and a camera securement mechanism 12b for combining under pressure with an edge of an objective of the camera. The camera securement mechanism 12b can in principle also be connected with a separate, preferably annular-shaped bottom plate, which, in turn, subsequently supports the pot-shaped endoscope reception 13.

As FIGS. 1c, 1d and 1e show especially clearly, the edge region 13c of the endoscope reception 13 is encompassed by an assembly group which, in this embodiment example, is constituted of jaws 15, 16, 17 resting on the edge region 13c, an attachment 18 with annular-shaped cover 18a and a circumferential margin 18b, extending perpendicularly from the outer margin of cover 18a in the proximal direction P beyond the position of the edge region 13c, which forms the lateral outer wall of the endoscope coupler 1, as well as of an annulus 19, which is formed, in this example, with three local projections 19a, extending in the distal direction D and in contact on the underside of the edge region 13c, which annulus 19 is in contact in the radial direction on the outer side of the circumferential side wall 13b. Connected with this assembly is further an operating element 20 which, in the depicted example, is in practice realized by being formed onto the attachment 18 in the transition region between cover 18a and circumferential margin 18b.

For the formation of the assembly, the annulus 19 is connected with the margin 18b of attachment 18, which in this example is carried out using bolts 32, and the jaws 15, 16, 17 are each in their end region connected with first pins 21, 22, 23, which, as can be seen for example in the depiction of FIG. 1a or 1d, extend parallel to the direction of introduction of the endoscope head 90, with the annular-shaped cover 18a, wherein the support of pins 20, 21, 22 in jaws 15, 16, 17 and cover 18a is, however, implemented such that a rotation is possible. Accordingly, jaws 15, 16, 17 are each rotatable about an axis extending parallel to the direction of introduction of endoscope head 90.

The above described assembly is fundamentally disposed rotatably relative to the endoscope reception 13, the extent to which this movement is possible, is however limited thereby that in each instance at the other end of jaws 15, 16, 17 which is the end at which the first pins 21, 22, 23 are disposed, second pins 24, 25, 26, visible for example in FIG. 1a or 1e, are provided which are each guided in a guide groove 27, 28, 29 worked-in on the distal side of edge region 13c and are loaded with the force of a spring 31, visible in FIG. 1a as well as 3b, 4b and 5b. The spring 31 is mounted between a projection 19a and a bearing section 13d and acts as a compression spring which acts counter to a relative turning between the above described assembly and the endoscope reception 13.

The opening of the annular-shaped cover 18a is aligned with the endoscope head-receiving region 14 and defines an access 30 thereto, which is formed by the spatial region of the opening between the upper side, defining the distal end 2 of the endoscope coupler 1, of the annular-shaped cover 18a, and the distal upper side of edge region 13c.

The depiction of FIG. 1b shows already that the jaw 15 comprises a region 115 which projects into the access 30 and in this way blocks it. Point 125, projecting furthest into access 30, is adjoined on the one hand by a distal section 126 of the region 115 projecting into the access 30, in which the jaw 15 tapers in the direction toward the distal end 3 of endoscope coupler 1, wherein the distal end of region 115 is flush with the inner margin of the annular-shaped cover 18a. On the other hand, starting from this point 125, a proximal section 127 of the region 115 projecting into access 30, is available which tapers more steeply in the direction toward the proximal end 2 of the endoscope coupler 1 than does the distal section 126 of the region 115 projecting into the access 30.

Based on FIGS. 2 to 5b, the mechanism of action of the endoscope coupler 1 will now be described in detail. For this purpose, in FIG. 2a schematic depiction of the initial state during the coupling of an endoscope coupler 1 and an endoscope head 90 of an endoscope to be coupled with the endoscope coupler 1 is shown before the coupling, in FIGS. 3a and 3b the situation before the coupling of an endoscope head 90, in FIGS. 4a and 4b the situation during which the endoscope head 90 is just being coupled, and in FIGS. 5a and 5b the situation after the coupling of the endoscope head 90.

Figure 3B:
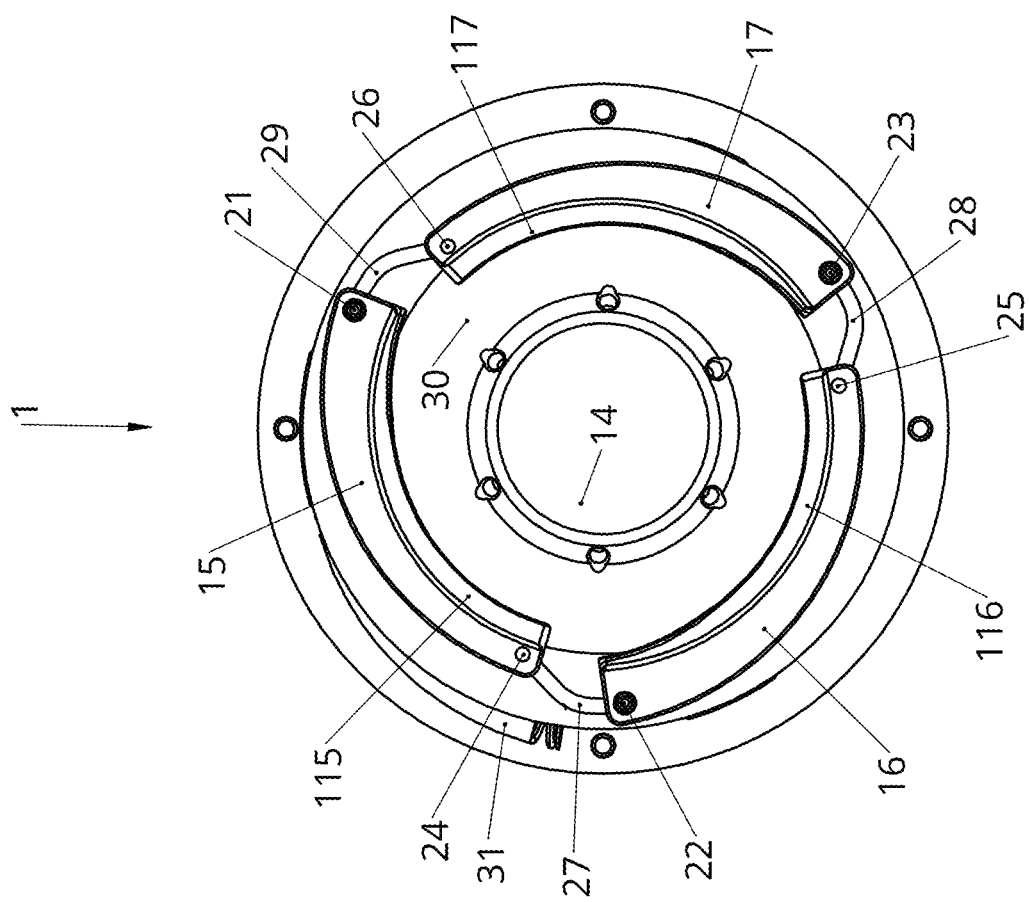
FIG. 3b: a second view of the endoscope coupler of FIG. 3a, however without endoscope head and without cover annulus, before the coupling.
Figure 4B:
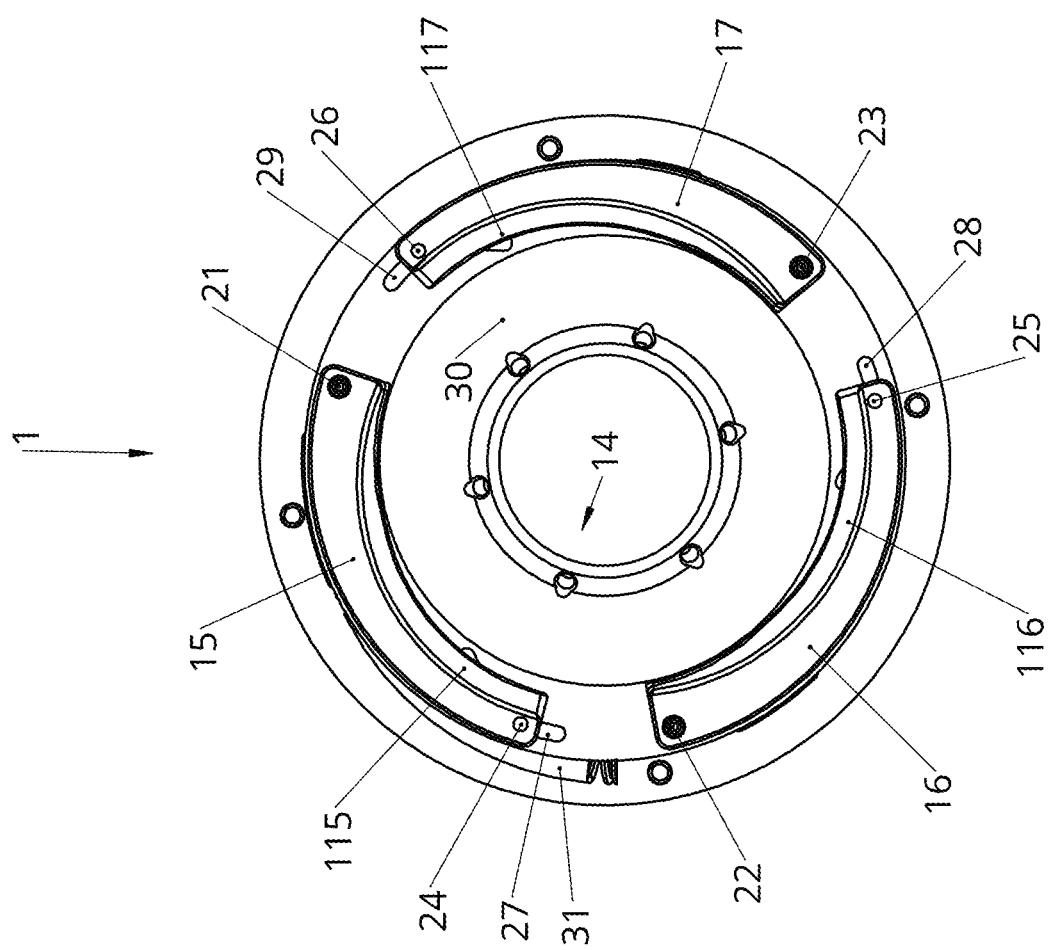
FIG. 4b: a second view of the endoscope coupler of FIG. 4a, however without endoscope head and without cover annulus, during the coupling.
Figure 5B:
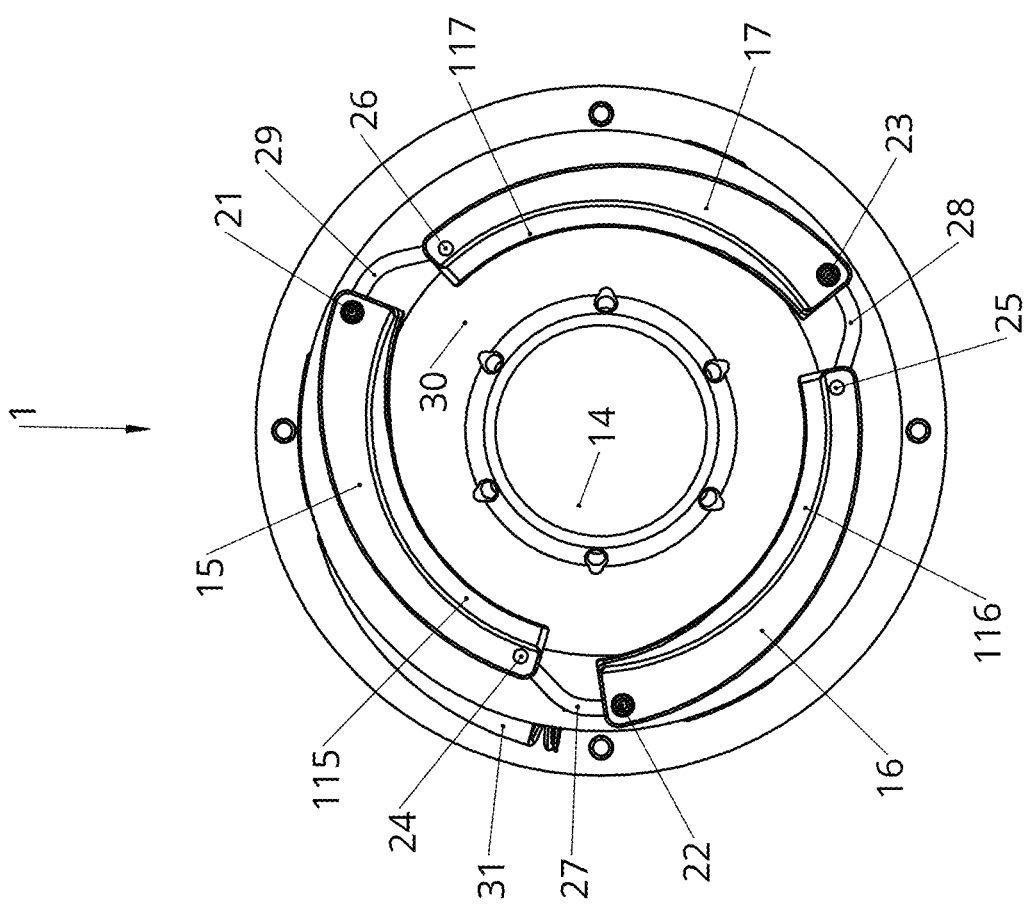
FIG. 5b: a second view of the endoscope coupler of FIG. 5a, however without endoscope head and without cover annulus, in the coupled state.

The endoscope coupler 1 is depicted in all of FIGS. 3a, 4a and 5a with a partially transparent cover 18a and endoscope head 90, such that consideration of the position of the jaws 15, 16, 17, which would otherwise in these aspects actually be obscured in these Figures, is enabled, and in the FIGS. 3b, 4b and 5b the endoscope coupler 1 is depicted in each instance without the annular-shaped cover 18a, in order to facilitate the comprehension in particular of the movement of the jaws 15, 16, 17 through the view into the interior of the endoscope coupler 1. This configuration is denoted in the following as the opened endoscope coupler 1.

Important for the correct understanding of these Figures is herein necessary to be remember that jaws 15, 16, 17 move with the circumferential margin 18b, the annulus 19 connected thereto and the operating element 20 disposed on the circumferential margin 18b, while the pot-shaped endoscope reception 13, which is connected across the securement means 12a, 12b with the not depicted camera, remains stationary.

Figure 2:
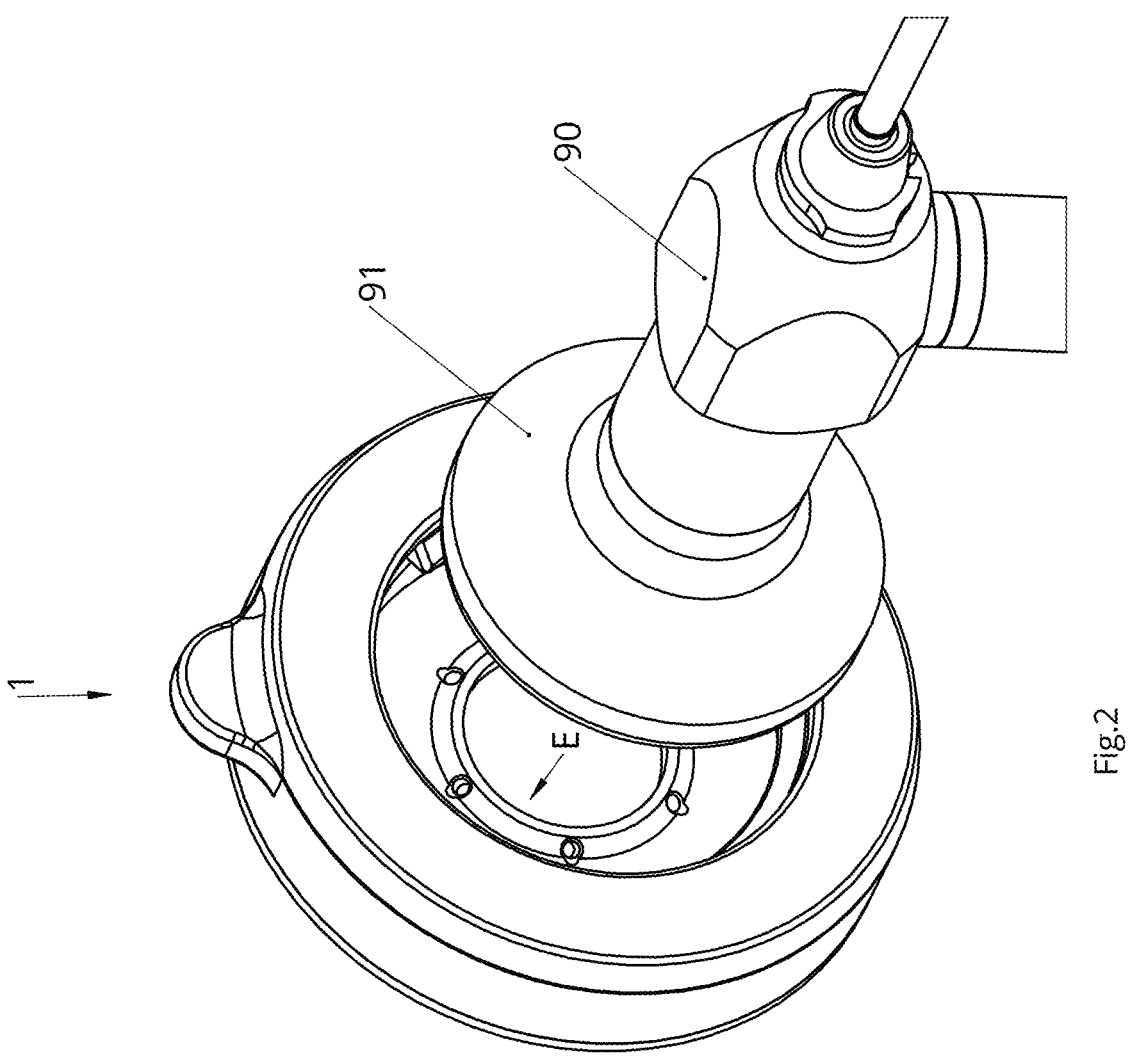
FIG. 2: a schematic representation of the initial state in the coupling of an endoscope coupler and of an endoscope head by means of an endoscope to be coupled with the endoscope coupler before the coupling.

FIG. 2 shows the opened endoscope coupler 1 and the endoscope head 90 with eye piece 91 in a possible initial position before the start of the coupling process. The direction of introduction E is indicated by an arrow. It extends from the endoscope coupler 1 in the proximal direction and thus toward its proximal end 2.

In FIG. 3b is especially well evident the state of the jaws 15, 16, 17 of the endoscope coupler 1 in this state: by reciprocal action of at least one spring 31 with the second pins 24, 25, 26, guided in the guide grooves 27, 28, 29, sections 115, 116, 117 are pressed into the access 30 and block it such that the [introduction of the] eye piece 91 of endoscope head 90, as can be especially well seen in FIG. 3a, into the endoscope head-receiving region 14 cannot take place without the reciprocal action with jaws 15, 16, 17 of the endoscope coupler 1.

If the endoscope head 90 with the proximal edge of the eye piece 91 is brought into contact with jaws 15, 16, 17, in particular their distal sections 126 in the proximity of the regions 115, 116, 117 projecting into the access 30, and pressure is exerted that is strong enough to overcome the spring force, jaws 15, 16, 17 recede under guidance in the particular guide groove 27, 28, 29. Due to the connection of jaws 15, 16, 17 across the first pins 21, 22, 23 to the not shown annular cover 18a, this leads to the fact that its entire assembly, including the circumferential margin 18b, of annulus 19 and the operating element 20 rotate, while the regions 115, 116, 117, projecting into access 30, are pressed increasingly further out of the access 30 until, lastly, the state shown in FIGS. 4a and 4b is reached in which the endoscope head 90 with the eye piece 91 starts entering into the endoscope head-receiving region 14. In this state the spring 31 is maximally stressed, i.e. it is maximally compressed since it is configured as a compression spring.

As soon as the outer margin of eye piece 91 has passed the point 125 that projects furthest into the access 30, of regions 115, 116, 117 of jaws 15, 16, 17, it arrives in the proximal section 127 of regions 115, 116, 117 and the jaws 15, 16, 17, driven by the spring force, start to close again such that the regions 115, 116, 117 of jaws 15, 16, 17 start to enter access 30 again. Thereby the outer margin of eye piece 91 is pressed onto the bottom 13a of the endoscope reception 13. The endoscope head 90 is therewith clamped to the bottom 13a and can no longer readily leave the endoscope head-receiving region 14, as is illustrated in FIGS. 5a and 5.

To be able nevertheless to enable this at the end of the use of the endoscope, with the aid of the actuation element 20 the assembly with circumferential margin 18b, annulus 19, annular-shaped cover 18a and jaws disposed thereon by means of the first pins 21, 22, 23, can rotate in the same direction counter to the spring force of the not shown spring 31 into which it moves during the introduction of the endoscope head 90 due to the reciprocal action between endoscope head 90 and jaws 15, 16, 16. This forces a movement of jaws 15, 16, 17 in the guide groove 27, 28, 29, which pulls the regions 115, 116, 117 out of access 30. The endoscope head 90 is released and can be removed again.

LIST OF REFERENCE NUMBERS

1 Endoscope coupler
2 Proximal end
3 Distal end
12a Camera securement mechanism
12b Camera securement mechanism
13 Endoscope reception
13a Bottom
13b Side wall
13c Edge region
13d Bearing section
14 Endoscope head-receiving region
15, 16, 17 Jaw
18 Attachment
18a Cover
18b Margin
19 Annulus
19a Projection
20 Operating element
21, 22, 23 First pin
24, 25, 26 Second pin
27, 28, 29 Guide groove
30 Access
31 Spring
32 Bolt
90 Endoscope head
91 Eye piece
115, 116, 117 Region
125 Point
126 Distal section
127 Proximal section
P Proximal direction
D Distal direction
E Direction of introduction
A-A Sectional line
B-B Sectional line
C-C Sectional line

The invention claimed is:

1. An endoscope coupler for a camera, comprising:
a proximal end of the endoscope coupler for disposition of the endoscope coupler on the camera, with a camera securement region and with an endoscope head-receiving region for at least partial reception of an endoscope head when the endoscope is coupled with the camera,
wherein the endoscope head-receiving region is accessible across an access of the endoscope head from a direction of a distal end of the endoscope coupler, and with an endoscope-fixing mechanism for the securement of the endoscope on the endoscope coupler,
wherein the endoscope-fixing mechanism comprises at least one movably supported jaw loaded with a spring force such that at least one region of the jaw is pressed into the access and blocks the access prior to receiving an endoscope,
wherein at least a region of the jaw projecting into the access is formed such that a distal section of the region of the jaw tapers in the direction toward the distal end of the endoscope coupler such that a pressure exerted on the distal section of the region of the jaw in the direction toward the proximal end of the endoscope coupler generates a force that counteracts the spring force that pressed at least one region of the jaw into the access and blocked the access,
wherein the regions of the jaw projecting into the access are movable out of the access to release a coupled endoscope; and
wherein rotation of the endoscope coupler with respect to the endoscope head-receiving region reduces the spring force that loads the jaw.

2. The endoscope coupler as in claim 1, wherein at least the region of the jaw projecting into the access is formed such that a proximal section of the region of the jaw is tapered more steeply in the direction toward the proximal end of the endoscope coupler than is the distal section in the direction toward the distal end of the endoscope coupler.

3. The endoscope coupler as in claim 1, wherein the movably supported jaw is supported such that the movably supported jaw is rotatable about an axis extending parallel to a direction of introduction of the endoscope head.

4. The endoscope coupler as in claim 3, wherein the movably supported jaw is supported such that the movably supported jaw is displaceable in a guide groove.

5. The endoscope coupler as in claim 4, wherein the spring force loading takes place through at least one spring disposed in the guide groove.

6. The endoscope coupler as in claim 1, wherein the movably supported jaw is supported by a first pin which projects beyond the movably supported jaw either only in the direction toward the distal end of the endoscope or only in the direction toward the proximal end of the endoscope coupler, such that the movably supported jaw is rotatable about an axis extending parallel to a direction of introduction of the endoscope head.

7. The endoscope coupler as in claim 6, wherein the movably supported jaw supported displaceably in the guide groove is implemented through a second pin which only projects beyond the jaw in a direction that is opposite to the direction in which the first pin, through which the supported jaw takes place that is rotatable about the axis extending parallel to the direction of introduction of the endoscope head, projects beyond the jaw.

8. A camera with an endoscope coupler, the endoscope coupler comprising:
a proximal end of the endoscope coupler for disposition of the endoscope coupler on the camera, with a camera attachment and with an endoscope head-receiving region for at least partial reception of an endoscope head when an endoscope is coupled with the camera,
wherein the endoscope head-receiving region is accessible across an access of the endoscope head from a direction of a distal end of the endoscope coupler, and with an endoscope-fixing mechanism for a securement of the endoscope on the endoscope coupler,
wherein the endoscope-fixing mechanism comprises at least one movably supported jaw loaded with a spring force such that at least one region of the jaw is pressed into the access and blocks the access prior to receiving an endoscope,
wherein at least the region of the jaw projecting into the access is formed such that a distal section of the region of the jaw tapers in the direction toward the distal end of the endoscope coupler such that a pressure exerted on the distal section of the region of the jaw in a direction toward the proximal end of the endoscope coupler generates a force that counteracts the spring force that pressed at least one region of the jaw into the access and blocked the access,
wherein rotation of the endoscope coupler with respect to the endoscope head-receiving region reduces the spring force that loads the jaw, and
wherein, when the spring force that loads the jaw is reduced, the regions of the jaw projecting into the access are movable out of the access.

9. The camera as in claim 8, wherein the endoscope coupler is fixedly connected with the camera.

10. The camera as in claim 8, wherein a portion of an optical system of the camera is disposed on the endoscope coupler.

* * * * *